(12) United States Patent
Ditzel et al.

(10) Patent No.: US 8,524,954 B2
(45) Date of Patent: Sep. 3, 2013

(54) HYDROGENATION OF ETHANOIC ACID TO PRODUCE ETHANOL

(75) Inventors: Evert Jan Ditzel, Goole (GB); Sander Gaemers, Skirlaugh (GB); John Glenn Sunley, Cottingham (GB)

(73) Assignee: BP P.L.C., London (GB)

( * ) Notice: Subject to any disclaimer, the term of this patent is extended or adjusted under 35 U.S.C. 154(b) by 307 days.

(21) Appl. No.: 12/998,639

(22) PCT Filed: Nov. 10, 2009

(86) PCT No.: PCT/GB2009/002639
§ 371 (c)(1),
(2), (4) Date: May 12, 2011

(87) PCT Pub. No.: WO2010/055285
PCT Pub. Date: May 20, 2010

(65) Prior Publication Data
US 2011/0224462 A1    Sep. 15, 2011

(30) Foreign Application Priority Data
Nov. 13, 2008    (EP) .................................... 08253723

(51) Int. Cl.
*C07C 29/152*    (2006.01)
*C07C 29/157*    (2006.01)
*C07C 27/06*    (2006.01)

(52) U.S. Cl.
USPC ........................................................ 568/885

(58) Field of Classification Search
USPC ................................................ 568/885, 909
See application file for complete search history.

(56) References Cited

U.S. PATENT DOCUMENTS

| | | |
|---|---|---|
| 3,326,956 A | 6/1967 | Davies et al. |
| 3,772,380 A | 11/1973 | Paulik et al. |
| 4,122,110 A | 10/1978 | Sugier et al. |
| 4,831,060 A | 5/1989 | Stevens et al. |
| 5,659,077 A | 8/1997 | McFarlan |

FOREIGN PATENT DOCUMENTS

| | | |
|---|---|---|
| EP | 0 030 110 | 6/1981 |
| EP | 0 303 438 A2 | 2/1989 |
| EP | 0 643 034 A1 | 3/1995 |
| GB | 1 234 641 | 6/1971 |
| GB | 1 234 642 | 6/1971 |
| GB | 1 276 326 | 6/1972 |
| WO | WO 83/03409 | 10/1983 |
| WO | WO 83/03409 A1 | 10/1983 |
| WO | WO 99/02254 A1 | 1/1999 |
| WO | WO 00/23689 A1 | 4/2000 |
| WO | WO 2006/107187 A1 | 10/2006 |

OTHER PUBLICATIONS

PCT Notification Concerning Transmittal of International Preliminary Report on Patentability; Form PCT/IB/326, Int'l Application No. PCT/GB2009/002639, filed Nov. 10, 2009 (7 pgs).
Elliott, D.J., et al; "Mechanism of Ethanol Formation from Synthesis Gas over CuO/ZnO/Al$_2$O$_3$"; *Journal of Catalysis*, vol. 114, pp. 90-99 (1988).
Gunardson, H.H., et al; "Produce CO-rich synthesis gas"; *Hydrocarbon Processing*; vol. 78:4, pp. 87-90 and 92-93 (1999).
Bourbonneux, G.; "Fisher-Tropsch synthesis gas production routes"; *Pétrole et Techniques*, No. 415, pp. 86-93 (1998).
Mayer, J., et al; "A Microstructured Reactor for the Catalytic Partial Oxidation of Methane to Syngas"; *IMRET 3: Proceedings of the Third International Conference on Microreaction Technology*, ed. W. Ehrfeld, Springer Verlag, pp. 187-196 (1999).
Linthwaite, M., et al; "Compact reformers in gas conversion"; *Hydrocarbon Engineering*; vol. 5:5, pp. 67-69 (2000).
*Hydrocarbon Processing*, vol. 79:9, p. 34 (2000).
International Search Report for PCT/GB2009/002639, dated Apr. 14, 2010.
Written Opinion for PCT/GB2009/002639, dated Apr. 14, 2010.

*Primary Examiner* — Sikarl Witherspoon
(74) *Attorney, Agent, or Firm* — Nixon & Vanderhye

(57) ABSTRACT

The present invention relates to a process for producing methanol and ethanol, wherein the methanol is produced from synthesis gas and the ethanol is produced via the hydrogenation of an ethanoic acid feed; characterized in that the hydrogenation of the ethanoic acid feed is carried out within the same alcohol synthesis unit and in the presence of the same catalyst(s) that is used to produce the methanol from the synthesis gas and wherein the feed introduced to the alcohol synthesis unit comprises synthesis gas and ethanoic acid.

22 Claims, 1 Drawing Sheet

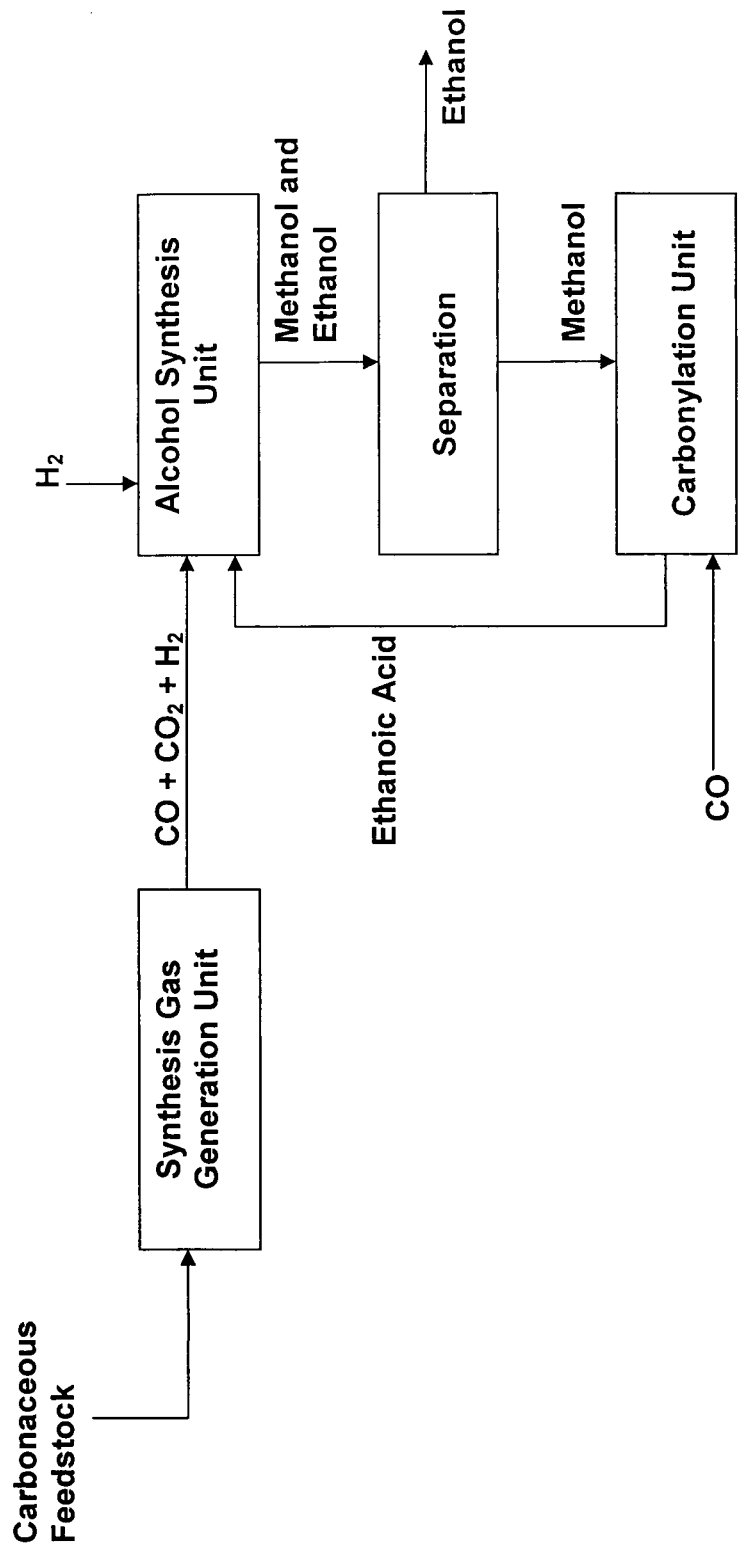

HYDROGENATION OF ETHANOIC ACID TO PRODUCE ETHANOL

This application is the U.S. national phase of International Application No. PCT/GB2009/002639 filed 10 Nov. 2009 which designated the U.S. and claims priority to EP 08253723.4 filed 13 Nov. 2008, the entire contents of each of which are hereby incorporated by reference.

The present invention relates to the production of ethanol.

In particular, the present invention concerns a process for the production of ethanol (and optionally methanol) from synthesis gas and ethanoic acid; wherein the ethanoic acid is hydrogenated to produce ethanol within the same alcohol synthesis unit and in the presence of the same catalyst(s) that is used to produce methanol from the synthesis gas.

In recent years, increased use and demand for alcohols such as methanol, ethanol and higher alcohols has led to a greater interest in processes relating to alcohol production. The alcohols may be produced by the fermentation of, for example, sugars and/or cellulosic materials.

Alternatively alcohols, such as ethanol, may be produced from synthesis gas. Synthesis gas refers to a combination of $H_2$ and carbon oxides produced in a synthesis gas plant from a carbon source such as natural gas, petroleum liquids, biomass and other carbonaceous materials including coal, recycled plastics, municipal wastes, or any organic material. Thus, alcohol and alcohol derivatives may provide non-petroleum based routes for the production of valuable chemicals and fuels.

Generally, the production of alcohols, for example methanol, takes place via three process steps: synthesis gas preparation, methanol synthesis, and methanol purification. In the synthesis gas preparation step, an additional stage may be employed whereby the feedstock is treated, e.g. the feedstock is purified to remove sulphur and other potential catalyst poisons prior to being converted into synthesis gas. This treatment can also be conducted after synthesis gas preparation; for example, when coal or biomass is employed.

The reaction to produce alcohol(s) from synthesis gas is generally exothermic. The formation of $C_2$ and $C_{2+}$ alcohols is believed to proceed via the formation of methanol for modified methanol catalysts and cobalt molybdenum sulphide catalysts. However, the production of methanol is equilibrium-limited and thus requires high pressures in order to achieve viable yields. Hence, pressure can be used to increase the yield, as the reaction which produces methanol exhibits a decrease in volume, as disclosed in U.S. Pat. No. 3,326,956.

A low-pressure, copper-based methanol synthesis catalyst is commercially available from suppliers such as BASF, Johnson Matthey, and Haldor-Topsoe. Methanol yields from copper-based catalysts are generally over 99.5% of the converted $CO+CO_2$ present. Water is a by-product of the conversion of $CO_2$ to methanol and the conversion of CO synthesis gas to $C_2$ and $C_{2+}$ oxygenates. In the presence of an active water-gas shift catalyst, such as a methanol catalyst or a cobalt molybdenum catalyst the water equilibrates with the CO to give $CO_2$ and $H_2$. A paper entitled, "Selection of Technology for Large Methanol Plants," by Helge Holm-Larsen, presented at the 1994 World Methanol Conference, Nov. 30-Dec. 1, 1994, in Geneva, Switzerland, reviews the developments in methanol production and shows how further reduction in costs of methanol production will result in the construction of very large plants with capacities approaching 10,000 t per day.

Other processes for the production of $C_2$ and $C_{2+}$ alcohol(s), include the processes described hereinafter;

WO 8303409 describes a process whereby ethanol is produced by carbonylation of methanol by reaction with CO in the presence of a carbonylation catalyst to form ethanoic acid which is then converted to an ethanoate ester followed by hydrogenolysis of the ethanoate ester formed to give ethanol or a mixture of ethanol and another alcohol which can be separated by distillation. Carbonylation can be effected using a $CO/H_2$ mixture and hydrogenolysis can similarly be conducted in the presence of CO, leading to the possibility of circulating gas between the carbonylation and hydrogenolysis zones with synthesis gas, preferably a 2:1 $H_2$:CO molar mixture being used as make up gas.

U.S. Pat. No. 4,122,110 relates to a process for manufacturing alcohols, particularly linear saturated primary alcohols, by reacting CO with $H_2$ at a pressure between 2 and 25 MPa and a temperature between 150 and 400° C., in the presence of a catalyst, characterized in that the catalyst contains at least 4 essential elements: (a) copper (b) cobalt (c) at least one element M selected from chromium, iron, vanadium and manganese, and (d) at least one alkali metal.

U.S. Pat. No. 4,831,060 relates to the production of mixed alcohols from CO and $H_2$ gases using a catalyst, with optionally a co-catalyst, wherein the catalyst metals are molybdenum, tungsten or rhenium, and the co-catalyst metals are cobalt, nickel or iron. The catalyst is promoted with a Fischer-Tropsch promoter like an alkali or alkaline earth series metal or a smaller amount of thorium and is further treated by sulphiding. The composition of the mixed alcohols fraction can be selected by selecting the extent of intimate contact among the catalytic components.

Journal of Catalysis, 1988, 114, 90-99 discloses a mechanism of ethanol formation from synthesis gas over $CuO/ZnO/Al_2O_3$. The formation of ethanol from CO and $H_2$ over a CuO/ZnO methanol catalyst is studied in a fixed-bed microreactor by measuring the isotopic distribution of the carbon in the product ethanol when isotopically-enriched $^{13}C$ methanol was added to the feed.

As the importance of ethanol is ever increasing in today's world, so is the need and desire to produce ethanol from a carbonaceous feedstock with a higher carbon efficiency, a higher conversion and an improved productivity and selectivity.

The present invention provides a process that can allow one to produce ethanol from a carbonaceous feedstock. Moreover, the present invention provides a process that can allow one to produce ethanol from a carbonaceous feedstock, with an improved carbon efficiency and/or a higher selectivity and/or a more productive conversion to ethanol. Hence, the present invention can provide a process that allows one to produce ethanol from a carbonaceous feedstock, with an improved carbon efficiency, a higher selectivity and, in particular, with a more productive conversion to ethanol.

FIG. 1 represents an embodiment of a process scheme according to an embodiment of the present invention, wherein the references correspond to those used in the present description and appending claims.

Thus, the present invention provides a process for producing methanol and ethanol, wherein the methanol is produced from synthesis gas and the ethanol is produced via the hydrogenation of an ethanoic acid feed; characterised in that the hydrogenation of the ethanoic acid feed is carried out within the same alcohol synthesis unit and in the presence of the same catalyst(s) that is used to produce the methanol from the synthesis gas and wherein the feed introduced to the alcohol synthesis unit comprises synthesis gas and ethanoic acid.

The present invention further provides a process for the conversion of synthesis gas to ethanol, characterised by the process comprising the following steps:

1) introducing synthesis gas and ethanoic acid into an alcohol synthesis unit to produce methanol and ethanol, wherein the methanol is produced from synthesis gas and the ethanol is produced via the hydrogenation of the ethanoic acid feed, and wherein the hydrogenation of the ethanoic acid feed is carried out within the same alcohol synthesis unit and in the presence of the same catalyst(s) that is used to produce the methanol from the synthesis gas,
2) separating the methanol from the ethanol of step 1,
3) introducing methanol, from step 2, and CO into a carbonylation unit in the presence of a methanol carbonylation catalyst, to produce ethanoic acid,
4) feeding ethanoic acid, produced in step 3, into the alcohol synthesis unit of step 1, and
5) recovering ethanol from step 2.

The present invention yet further provides a process for the conversion of a carbonaceous feedstock(s) into ethanol, characterised by the following steps:

1) introducing a carbonaceous feedstock into a synthesis gas reactor to produce synthesis gas,
2) introducing synthesis gas, from step 1, and ethanoic acid into an alcohol synthesis unit to produce methanol and ethanol, wherein the methanol is produced from synthesis gas and the ethanol is produced via the hydrogenation of the ethanoic acid feed, and wherein the hydrogenation of the ethanoic acid feed is carried out within the same alcohol synthesis unit and in the presence of the same catalyst(s) that is used to produce the methanol from the synthesis gas,
3) separating the methanol from the ethanol of step 2,
4) introducing methanol, from step 3, and CO, into a carbonylation unit in the presence of a methanol carbonylation catalyst, to produce ethanoic acid,
5) feeding ethanoic acid, produced in step 4, into the alcohol synthesis unit of step 2, and
6) recovering ethanol from step 3.

For the purposes of the present invention and appending claims the following terms are defined hereinafter:

The 'dew point temperature' is a threshold temperature, for example, for a given pure component or mixture of components, at a given pressure, if the system temperature is raised to above the dew point temperature, the mixture will exist as a dry gas. Likewise below the dew point temperature, the mixture will exist as a vapour containing some liquid.

'Gas hourly space velocity' (GHSV) is defined as the volume of gas fed per unit volume of catalyst per hour, at standard temperature (0° C.) and pressure (0.101325 MPa).

'Liquid hourly space velocity' (LHSV) is defined as the volume of liquid fed per unit volume of catalyst per hour.

According to one aspect of the present invention, the synthesis gas feedstock, a mixture of carbon oxide(s) and $H_2$, that is used to produce the methanol feed stream, is preferably produced from a carbonaceous feedstock.

The carbonaceous feedstock is preferably a material such as biomass, plastic, naphtha, refinery bottoms, crude synthesis gas (from underground coal gasification or biomass gasification), smelter off gas, municipal waste, coal bed methane, coal, and/or natural gas, with coal and natural gas being the preferred sources. To one skilled in the art a combination of sources can also be used, for example coal and natural gas to advantageously increase the $H_2$ to carbon ratio.

Natural gas commonly contains a range of hydrocarbons (e.g. $C_1$-$C_3$ alkanes), in which methane predominates. In addition to this, natural gas will usually contain nitrogen, $CO_2$ and sulphur compounds. Preferably the nitrogen content of the feedstock is less than 40 mol %, more preferably less than 10 mol % and most preferably less than 2 mol %.

Processes for producing synthesis gas, in a synthesis gas plant, are well known. Each method has its advantages and disadvantages, and the choice of using a particular reforming process over another is governed by economic and available feed stream considerations, as well as by the desire to obtain the optimum ($H_2$—$CO_2$):($CO$+$CO_2$) molar ratio in the resulting synthesis gas that is suitable for further chemical processing. A discussion of the available synthesis gas production technologies is provided in both Hydrocarbon Processing, 1999, 78:4, 87-90, and 92-93 and Petrole et Techniques, 1998, 415, 86-93, and are both hereby incorporated by reference.

It is also known that the synthesis gas may be obtained by catalytic partial oxidation of hydrocarbonaceous material in a microstructured reactor as exemplified in IMRET 3: Proceedings of the Third International Conference on Microreaction Technology, ed. W. Ehrfeld, Springer Verlag, 1999, pages 187-196. Alternatively, the synthesis gas may be obtained by short contact time catalytic partial oxidation of hydrocarbonaceous feedstocks as described in EP 0303438. The synthesis gas can also be obtained via a 'compact reformer' process as described in Hydrocarbon Engineering, 2000, 5:5, 67-69; Hydrocarbon Processing, 2000, 79:9, 34; Today's Refinery, 2000, 15:8, 9; WO 9902254; and WO 0023689.

Typically, for commercial synthesis gas production the pressure at which the synthesis gas is produced from a steam reformer ranges from approximately 0.1 to 10 MPa, preferably 2 to 3 MPa and the temperatures at which the synthesis gas exits the reformer ranges from approximately 700 to 1000° C. Likewise, for commercial synthesis gas production the pressure at which the synthesis gas is produced from an auto-thermal reformer ranges from approximately 0.1 to 10 MPa, preferably 2 to 5 MPa and the temperatures at which the synthesis gas exits the reformer ranges from approximately 700 to 1300° C. Where the high temperatures are necessary in order to produce a favourable equilibrium for synthesis gas production, and to avoid metallurgy problems associated with carbon dusting. The synthesis gas contains a molar ratio of ($H_2$—$CO_2$):($CO$+$CO_2$) ranging from 0.8 to 3.0, which is dependent on the carbonaceous feedstock(s) and the method of reforming used. For example, when natural gas is used as the carbonaceous feedstock for steam reforming, the synthesis gas obtained usually has a maximum ($H_2$—$CO_2$):($CO$+$CO_2$) ratio of 3.0. However, when natural gas is used as the carbonaceous feedstock for auto-thermal reforming, the synthesis gas obtained usually has a ($H_2$—$CO_2$):($CO$+$CO_2$) ratio of 1.5.

According to a preferred embodiment of the present invention, the molar ratio, ($H_2$—$CO_2$):($CO$+$CO_2$), of the synthesis gas stream exiting the synthesis gas generation unit(s) is greater than 1.6, more preferably greater than 1.8 and most preferably greater than 2.0. Preferably, the molar ratio, ($H_2$—$CO_2$):($CO$+$CO_2$), of said synthesis gas stream exiting the synthesis gas generation unit(s) is less than 3.0, preferably less than 2.75, more preferably less than 2.4 and most preferably less than 2.2.

According to another embodiment of this invention when the carbonaceous feedstock used for synthesis gas generation is not an aliphatic hydrocarbon (e.g. coal, aromatic material, biomass) the molar ratio ($H_2$—$CO_2$):($CO$+$CO_2$) of the exit synthesis gas is preferably adjusted to the target value by the addition of $H_2$ or the removal of $CO_2$.

$CO_2$ may be removed by the use of a simple, yet effective, separation method known to those skilled in the art, for example, a "membrane separation method". Such membrane technologies can be found in 'Purification and Recovery Options for Gasification' D. J. Kubek, E. Polla, F. P. Witcher, UOP, 1996.

Alternatively, $CO_2$ may be recovered and removed by any suitable method(s) known to those skilled in the art, for example, by reacting with amines; performing a methanol wash (i.e. the RECTISOL process) and/or by using hot potassium carbonate (e.g. the BENFIELD process).

According to a preferred embodiment of the present invention, the exit stream obtained from the synthesis gas reactor (e.g. using a steam reformer), comprises essentially a mixture of carbon oxide(s) and $H_2$. It can also comprise water, nitrogen and traces of unconverted hydrocarbons (e.g. $C_1$-$C_3$ alkanes).

According to a preferred embodiment of the present invention, during synthesis gas generation, an additional stage may be employed whereby the feedstock is first purified to remove sulphur and other potential catalyst poisons (such as halides or metals e.g. mercury) prior to being converted into synthesis gas; alternatively this treatment can also be performed after synthesis gas preparation for example, when coal or biomass are used.

According to the present invention, synthesis gas and ethanoic acid are introduced into an alcohol synthesis unit to produce a stream comprising methanol and ethanol, in addition to unreacted ethanoic acid. The synthesis gas feed and the ethanoic acid feed may be introduced to the alcohol synthesis unit either as separate feed streams, a combined feed stream, or any combination of feed streams which comprise the components thereof. In one specific embodiment of the present invention, the synthesis gas and the ethanoic acid are introduced to the alcohol synthesis unit as separate feed streams. In another specific embodiment of the present invention, the synthesis gas and the ethanoic acid are introduced to the alcohol synthesis unit as a combined feed stream. According to a preferred embodiment of the present invention at least a part, preferably all, of said synthesis gas stream is produced by a synthesis gas generation process.

Additionally, by-products such as methane and higher alcohols may also be produced during alcohol synthesis (i.e. methanol and ethanol synthesis). According to a preferred embodiment of the present invention, the stream exiting the alcohol synthesis unit is subsequently purified to remove said by-products by any methods known to those in the art to obtain substantially pure methanol and ethanol products.

For the targeted production of ethanol the preferred molar ratio, ($H_2$—$CO_2$):($CO$+$CO_2$), of the fresh synthesis gas feed stream fed into the alcohol synthesis unit is greater than 3.0, more preferably greater than 4.0 and most preferably greater than 4.1. Preferably the molar ratio, ($H_2$—$CO_2$):($CO$+$CO_2$), of the fresh synthesis gas feed stream fed into the alcohol synthesis unit is less than 8.5, preferably less than 5.0 and most preferably less than 4.4. The Applicants have also unexpectedly found that the co-feed of CO and $CO_2$ into the alcohol synthesis unit was particularly beneficial to the selectivity of the process according to the present invention. Therefore $CO_2$ represents more than 1 vol %, preferably more than 2 vol % and most preferably more than 5 vol % of the total alcohol synthesis unit gas phase composition.

In order to obtain the aforementioned high synthesis gas molar ratios, additional $H_2$ typically needs to be added to the synthesis gas feed stream exiting the synthesis gas generation unit. Preferably, this additional $H_2$ is obtained from a synthesis gas generation stage. This is preferably performed by first removing $CO_2$ and water from the generated synthesis gas followed by a cryogenic separation to isolate the substantially pure CO from the $H_2$. Alternative methods of separation, such as membrane separation technologies can also be employed. Alternatively, said $H_2$ stream may also be obtained from another suitable source, such as another chemical process (e.g. off-gas from steel manufacture or electrolysis). Said $H_2$ stream(s) may still contain inert impurities such as methane, nitrogen, noble gases, water and $C_1$ to $C_4$ paraffinic hydrocarbons, which are preferably removed before use.

An added advantage of this aspect of the present invention, when compared to other processes in the field, is that the purification of the separated $H_2$ feed produced during synthesis gas generation has no requirement for the removal of carbon oxides. Indeed, this is advantageous when compared to a process with a separate hydrogenation stage for ethanoic acid where the carbon oxides act as poisons to the hydrogenation catalyst as well as increasing the formation of inert materials, thus necessitating an increased purge step.

The alcohol synthesis unit of the present invention comprises at least one reaction zone. According to a preferred embodiment of the present invention, the alcohol synthesis unit may be any reactor that is suitable for producing methanol and ethanol, for example a fluidised bed reactor or a fixed bed reactor, which can be run with or without external heat exchange equipments e.g. a multi-tubular reactor; or a fluidised bed reactor; or a void reactor.

Preferably the alcohol synthesis unit is operated at a temperature of more than 180° C., preferably more than 200° C. and most preferably more than 220° C.; and less than 290° C., preferably less than 280° C., more preferably less than 270° C. and most preferably less than 250° C. Preferably the alcohol synthesis unit is operated at pressure of more than 2 MPa and preferably more than 5 MPa; and less than 10 MPa and preferably less than 9 MPa. In fact, since methanol synthesis is an exothermic reaction, the chosen temperature of operation is governed by a balance of promoting the forward reaction (i.e. by not adversely affecting the equilibrium) and aiding the rate of conversion (i.e. higher productivity). The ethanol synthesis is also exothermic; however, in this case the chosen temperature of operation is governed by a balance of reaction rate and selectivity.

The GHSV for continuous operation may be in the range 50 to 50,000 $h^{-1}$, preferably from 1,000 to 30,000 $h^{-1}$, more preferably from 2,000 to 18,000 $h^{-1}$ and most preferably from 5,000 to 12,000 $h^{-1}$.

The ethanoic acid liquid substrate introduced into the alcohol synthesis unit preferably has an LHSV less than 10 $h^{-1}$, more preferably less than 5 $h^{-1}$ and most preferably less than 3 $h^{-1}$; for example, a typical LHSV for normal operation is approximately 1 $h^{-1}$.

A key feature of the present invention is that the synthesis of methanol from synthesis gas and the hydrogenation of ethanoic acid to ethanol occurs in the same alcohol synthesis unit. Therefore the catalyst for methanol synthesis from synthesis gas and the catalyst for ethanoic acid hydrogenation may be one and the same catalyst; or, alternatively, more than one catalyst may be employed in the alcohol synthesis unit. The catalyst, or catalysts, may be any suitable catalyst known to those skilled in the art to catalyse the synthesis of methanol from synthesis gas and those which are known to those skilled in the art to catalyse the hydrogenation of carboxylic acids and/or esters to alcohols.

For the avoidance of doubt, when it is hereinafter referred to as a mixture of a methanol synthesis catalyst and a hydrogenation catalyst, it also covers physical blends of the two catalysts and/or separate packed zones of the two catalysts in the same reactor(s); according to a preferred mode of operation, the hydrogenation catalyst is located downstream of the methanol synthesis catalyst; thus, according to a preferred embodiment of the present invention, the catalyst configuration of the alcohol synthesis unit is such that the stream(s) comprising CO, $H_2$ (or synthesis gas) and ethanoic acid, is first reacted in the presence of a methanol synthesis catalyst and subsequently reacted in the presence of a hydrogenation catalyst.

In one embodiment of the present invention, the alcohol synthesis unit catalyst is a methanol synthesis catalyst.

The catalyst for the alcohol synthesis unit can be chosen amongst traditional methanol synthesis catalysts selected from one of the two following groups:
  i. the high pressure zinc catalysts, composed of zinc oxide and a promoter; and
  ii. low pressure copper catalysts, composed of zinc oxide, copper oxide, and a promoter.

Suitable promoters for the methanol synthesis catalyst include cobalt and/or magnesium and/or chromium and/or aluminium compounds. A preferred methanol synthesis catalyst is a mixture of copper, zinc oxide, and a promoter such as chromia or alumina. The Applicants have unexpectedly found that said methanol synthesis catalyst demonstrated high hydrogenation activities.

According to a preferred embodiment of the present invention, the preferred catalyst used in the alcohol synthesis unit is either a hydrogenation catalyst or consists of a mixture of the above methanol synthesis catalyst together with a hydrogenation catalyst. The hydrogenation catalyst can be selected from the following:
  (i) a metal based catalyst, comprising of at least one metal from Group VIII of the periodic table (CAS version, for example iron, ruthenium, osmium, cobalt, rhodium, iridium, nickel, palladium, platinum) and at least one metal chosen from rhenium, tungsten and/or molybdenum; and optionally an additional metal, that is capable of alloying with said Group VIII metal;
  (ii) a copper-based catalyst (for example a copper chromite or a mixed copper metal oxide based catalyst wherein the second metal can be copper, zinc, zirconium or manganese), and
  (iii) mixtures thereof.

For the avoidance of doubt, by the term Group VIII of the periodic table (CAS version) it is meant the groups corresponding to Group 8 to 10 transition metals in the Periodic Table of Elements proposed by the IUPAC in 1991 and which is found, for example, in "CRC Handbook of Chemistry and Physics", 76th Edition (1995-1996), by David R. Lide, published by CRC Press Inc. (USA).

According to a preferred embodiment of the present invention, the hydrogenation catalyst (which may be mixed with the methanol synthesis catalyst) is a copper based catalyst, most preferably comprising copper and zinc.

All of the aforementioned hydrogenation catalysts may advantageously be supported on any suitable support known to those skilled in the art; non-limiting examples of such supports include carbon, silica, titania, clays, aluminas, zinc oxide, zirconia and mixed oxides. Preferably, the palladium based catalyst is supported on carbon. Preferably, the copper based catalyst is supported on zinc oxide.

According to one embodiment of the present invention, the catalyst used in the alcohol synthesis unit is a hydrogenation catalyst as described above, wherein said hydrogenation catalyst exhibits methanol synthesis activity.

According to another embodiment of the present invention, the catalyst comprises a methanol synthesis catalyst mixed with a hydrogenation catalyst, wherein the hydrogenation catalyst mixed with the methanol synthesis catalyst is a supported copper based catalyst, which is different from the methanol synthesis catalyst, which comprises copper and at least one promoter, such as cobalt and/or manganese and/or chromium, supported on zinc oxide.

According to a preferred embodiment of the present invention, the alcohol synthesis unit catalyst(s) is a copper based catalyst, most preferably comprising copper and zinc.

According to an aspect of the present invention, at least a part of the stream exiting the alcohol synthesis unit is passed through a separation unit (e.g. a separation column) to recover and collect a stream comprising ethanol and a stream comprising methanol.

This separation stage may be performed by any suitable means known to those skilled in the art, e.g. a sieve tray column, a packed column, a bubble cap column or a combination thereof.

Since methyl ethanoate and ethyl ethanoate can also be present in the exit stream from the alcohol synthesis unit, when such compounds are present in the exit stream, the following are preferred mode of operation(s):
  (i) methanol/methyl ethanoate mixture can be recovered and fed directly into the downstream carbonylation unit, and/or
  (ii) ethanol/ethyl ethanoate mixture can be recovered and recycled to the alcohol synthesis unit.

Additionally, by-products such as methane, ethane and other higher alcohols may also be produced during alcohol synthesis. According to a preferred embodiment of the present invention, the streams exiting the separation zone are subsequently purified to remove said by-products from the methanol and ethanol streams by any methods known to those skilled in the art.

According to an aspect of the present invention, at least a part of the aforementioned stream comprising methanol (and optionally methyl ethanoate) and CO are introduced into a carbonylation unit. Typically, the methanol and CO are introduced into the carbonylation unit as two separate feed streams. Preferably, at least part, more preferably all, of the methanol stream emanates from the aforementioned alcohol synthesis unit. However, said methanol stream may also emanate from another suitable source, such as a bio-fermentation process and/or pyrolysis (e.g. wood pyrolysis).

Preferably, at least a part of the CO stream is obtained from a synthesis gas generation stage. This is preferably performed by first removing $CO_2$ and water from the generated synthesis gas followed by a cryogenic separation to isolate the substantially pure CO from the $H_2$. A particular advantage according to the present invention is that both the $H_2$ fed to the alcohol synthesis unit and the CO fed to the carbonylation unit can be obtained from the same synthesis gas separation stage. Alternative methods of separation, such as membrane separation technologies can also be employed. Alternatively, the CO stream may also be obtained from another suitable source, such as another chemical process (e.g. off-gas from steel manufacture). Said CO stream may contain low levels of inert impurities.

There are many examples in the prior art which disclose carbonylation processes that can be suitably used in the present invention.

For example, such carbonylation processes can be made in the presence of iridium catalysts as described in U.S. Pat. No. 3,772,380. UK patent GB 1276326 also describes the preparation of mono-carboxylic acids by carbonylation of alcohols in the presence of rhodium or iridium catalysts, halogen promoters and water or an alcohol, ether or ester. UK patents GB 1234641 and GB 1234642 describe a process for the production of an organic acid by carbonylation of an alcohol in the presence of a noble metal catalyst selected from iridium, platinum, palladium, osmium and ruthenium and their compounds.

Suitable carbonylation processes that may be used in the present invention are the carbonylation of methanol and/or a reactive derivative thereof, in the presence of a rhodium or iridium catalyst system. Suitable reactive derivatives of methanol include methyl acetate and dimethyl ether.

According to a preferred embodiment of the present invention, the carbonylation process takes place in the presence of an iridium catalyst system. Said carbonylation process is preferably performed in the presence of at least a finite concentration of water with a catalyst system comprising:
(a) an iridium catalyst, (b) methyl iodide and (c) at least one metal promoter.

Suitable iridium catalyst systems for use in the carbonylation process can be found in EP 0643034 A1.

Preferably, the concentration of water in the liquid reaction composition of the carbonylation unit is in the range 0.1 to 15 wt %, more preferably 1 to 10 wt %, most preferably 1 to 6.5 wt %.

When iridium catalysts are used in the carbonylation process, the iridium catalyst in the liquid reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H2O$, $Ir_4(CO)_{12}$, iridium metal, $Ir_2O_3$, $IrO_2$, $Ir(acac)(CO)_2$, $Ir(acac)_3$, iridium ethanoate, $[Ir_3O(OAc)_6(H_2O)_3][OAc]$, and hexachloroiridic acid $[H_2IrCl_6]$, preferably, chloride-free complexes of iridium such as ethanoates, oxalates and acetoacetates which are soluble in one or more of the carbonylation reaction components such as water, alcohol and/or carboxylic acid. Particularly preferred is green iridium ethanoate which may be used in an ethanoic acid or aqueous ethanoic acid solution.

Preferably, the iridium carbonylation catalyst concentration in the liquid reaction composition is in the range 100 to 6000 ppm by weight of iridium, more preferably 700 to 3000 ppm by weight of iridium.

Suitable metal promoters are preferably selected from the group consisting of ruthenium, osmium, rhenium, cadmium, mercury, zinc, gallium, indium and tungsten, and are more preferably selected from ruthenium and osmium and most preferably is ruthenium. Preferably, the promoter is present in an effective amount up to the limit of its solubility in the liquid reaction composition and/or any liquid process streams recycled to the carbonylation unit from the ethanoic acid recovery stage. The promoter is suitably present in the liquid reaction composition at a molar ratio of promoter:iridium of [0.5 to 15]:1. A suitable metal promoter concentration is 400 to 5000 ppm by weight.

The promoter may be added to the liquid reaction composition for the carbonylation reaction in any suitable form which dissolves in the liquid reaction composition or is convertible to soluble form.

Examples of suitable ruthenium-containing compounds and osmium-containing compounds which may be used as sources of the metal promoter can be found in EP 0643034 A1.

Preferably, the concentration of methyl iodide in the liquid reaction composition is in the range 1 to 20 wt %, preferably 5 to 16 wt %.

The partial pressure of CO in the carbonylation unit is suitably in the range 0.1 to 7 MPa preferably 0.1 to 3.5 MPa and most preferably 0.1 to 1.5 MPa.

The pressure of the carbonylation reaction is suitably in the range 0.9 to 19.9 MPa, preferably 0.9 to 9.9 MPa, most preferably 1.4 to 4.9 MPa. The temperature of the carbonylation reaction is suitably in the range 100 to 300° C., preferably in the range 150 to 220° C.

Ethanoic acid may advantageously be used as a solvent for said carbonylation reaction.

The carbonylation unit of the present invention comprises at least one reaction zone where the carbonylation process occurs.

The carbonylation process of the present invention may be performed as a batch or continuous process, preferably as a continuous process and may be performed in any suitable reactor.

The ethanoic acid product may be recovered from the carbonylation liquid reaction composition by conventional techniques, such as by flash and fractional distillation stages. The liquid reaction composition may be subjected to a flash separation stage where a crude ethanoic acid is separated from a liquid fraction which contains the majority of the catalyst. The crude ethanoic acid can be purified to remove water, methyl iodide and methyl acetate by one or more distillation stages.

Preferably, the purified ethanoic acid contains less than 0.1 ppm wt of carbonylation catalyst, more preferably less than 0.05 ppm wt, most preferably less than 0.005 ppm wt.

According to a preferred embodiment of the present invention, at least a part, preferably all, of the ethanoic acid feed stream is produced by a carbonylation reaction; however, it may also be produced by another process, such as wood pyrolysis and/or as a by-product of a fermentation process to produce alcohol(s).

In one embodiment of the present invention, the ethanoic acid is fed to the alcohol synthesis unit in the presence of an inert solvent.

According to a preferred embodiment of the present invention, the ethanoic acid stream contains less than 20 mol % of water. More preferably, water represents between 0.5 and 20 mol %, preferably between 0.5 and 15 mol % and most preferably between 1 and 5 mol % of the total liquid feed (ethanoic acid and water) to the alcohol synthesis unit.

Where necessary, the ethanoic acid fed into the alcohol synthesis unit is preferably purified of sulphur and halide compounds.

The ethanoic acid feed is preferably vapourised prior to contacting the alcohol synthesis catalyst. The feed mixture, including any recycle streams, entering the alcohol synthesis unit (e.g. the synthesis gas, together with the ethanoic acid) is preferably more than 10° C., preferably more than 20° C. above its dew point temperature.

It should be noted that whilst all of the aforementioned temperature and pressure operating conditions form preferred embodiments of the present invention, they are not, by any means, intended to be limiting, and the present invention hereby includes any other pressure and temperature operating conditions that achieve the same effect.

One embodiment of the invention will now be illustrated with reference to FIG. 1.

In FIG. 1, a carbonaceous feedstock is fed to the synthesis gas generation unit wherein it is converted to a product stream which comprises synthesis gas (carbon oxide(s) and hydrogen). The synthesis gas produced in the synthesis gas generation unit, ethanoic acid, and additional hydrogen (if required) are passed to the alcohol synthesis unit wherein it is converted to a product stream comprising methanol and ethanol. The methanol and ethanol containing product stream are passed to a separation unit wherein the ethanol is removed as product. At least a portion of the methanol containing stream separated in the separation unit and carbon monoxide are passed to a carbonylation unit, wherein the methanol is carbonylated to produce ethanoic acid. At least a portion of the ethanoic acid stream produced in the carbonylation unit is then used as at least part of the ethanoic acid feedstream for the alcohol synthesis unit.

The present invention will now be illustrated by the following Example.

EXAMPLE

A sample of commercially available Katalco 51-8 pellets (ex Johnson Matthey plc.), with a composition of approximately 64 weight % CuO, 10 weight % $Al_2O_3$, 24 weight % ZnO and 2 weight % MgO, was used in the example. The pellets were crushed and sieved and particles in the size range 212-335 microns were used as the catalyst.

The reactor used for the examples was a pressure flow reactor unit consisting of 60 identical parallel isothermal co-current tubular reactors, as described in, for example, WO2006107187. The reactors were arranged in 4 blocks of 15 reactors, each block having an independent temperature control.

Into ten reactor tubes (two reactors tubes in Block 1, 3 reactor tubes in Block 2, 2 reactor tubes in Block 3, and 3 reactor tubes in Block 4), 50 micro litres of catalyst (designed to give GHSVs under reaction conditions of 10,000 was loaded onto a metal sinter having a pore size of 20 micrometers. The catalyst samples were heated at a ramp rate of 5° C./min. to 240° C. under 74.5 mole % $H_2$, 8.5 mole % $CO_2$, 7.5 mole % CO, 9.0 mole % $N_2$ and 0.5 mole % He at atmospheric pressure at a flow rate of 8.3 mL/hour per reactor tube, and held at 240° C. for 1 hour. The reactors were then pressurised to 85 barg and the system held at this condition for approximately 28.2 hours. At this stage, a series of temperature variation experiments were carried out in which the temperature of the reactors in each of the four blocks, designated as blocks 1 to 4, were altered as described in Table 1.

TABLE 1

| Block 1 | Block 2 | Block 3 | Block 4 | Duration (hrs) |
|---|---|---|---|---|
| 200° C. | 240° C. | 275° C. | 300° C. | 18.5 |
| 240° C. | 275° C. | 300° C. | 200° C. | 12.0 |
| 275° C. | 300° C. | 200° C. | 240° C. | 12.2 |
| 300° C. | 200° C. | 240° C. | 275° C. | 12.0 |

After the temperature variation described in Table 1 was complete, the temperature of all four blocks was adjusted to 240° C. and a liquid feed comprising 74.1 g of ethanoic acid (ethanoic acid used every else) dissolved in 350.9 g of cyclohexane was fed to the reactors in blocks 1 to 3 at a rate designed to give approximately 1.5 mole % of ethanoic acid in the total gas feed. To compensate for the volume of ethanoic acid and cyclohexane, the flow of nitrogen was reduced in the gas feed decreasing the concentration of nitrogen in the total gas feed from 9.0 mole % to approximately 4.6 mole %. Pure cyclohexane was fed to the reactors in block 4 at a third of the total rate of liquid feed to the reactors in blocks 1 to 3, and the flow of nitrogen was adjusted accordingly. The system was held under these conditions for 18.3 hours (from ca. 82.9 to 101.2 hours on stream) and then the liquid feeds were turned off and the nitrogen flow was increased to return the gas feed to its original composition. The system was held under these conditions for 16 hours (from ca. 101.2 to 117.2 hours on stream).

The exit streams from the reactors were passed in turn to two gas chromatographs; a Varian 4900 micro GC with three columns (Molecular sieve 5A, Porapak® Q, and CP-Wax-52), each equipped with a thermal conductivity detector, and an Interscience Trace GC with two columns (CP-Sil 5 and CP-Wax 52), each equipped with a flame ionisation detector.

Data from the seven reactors in Blocks 1 to 3 containing the catalyst were averaged for the time periods 82.9 to 101.2 hours and 101.2 to 117.2 hours, along with data from the three reactors in Block 4 averaged for the time period 82.9 to 101.2 hours and 101.2 to 117.2 hours, is provided in Table 2.

One reactor tube in each block was left empty to provide a reference and the only materials detected by the Interscience Trace GC during the period from 82.9 to 101.2 hours were cyclohexane and ethanoic acid. The data from the three blank reactors in blocks 1 to 3 were averaged over this time period to calculate that an ethanoic acid (AcOH) space time yield (STY) of 406 g/(l·h) would be observed if all of the ethanoic acid passed unreacted through 50 microlitres of catalyst.

Taking ethanol (EtOH), ethane ($C_2H_6$), methyl acetate (MeOAc), ethyl acetate (EtOAc) and acetaldehyde (MeOC(O)H) as being the products derived from ethanoic acid; for the averaged data, the ethanoic acid mass balance was 99.6%, the conversion of ethanoic acid was 99.99% and the selectivity of ethanoic acid to ethanol was 98.7%.

The data provided in Table 2 demonstrates that methanol is still produced during the period that ethanoic acid is being fed to the reactor. A comparison of the data from blocks 1-3 for 82.9-101.2 hours, with the data from block 4 for 101.2-117.2, shows that the products derived from ethanoic acid are primarily ethanol, ethane, methyl acetate, ethyl acetate and acetaldehyde. Comparison of the data from block 4 for 82.9-101.2 hours, with the data from block 4 for 101.2-117.2 hours, shows that the addition of cyclohexane has little effect.

TABLE 2

| | MeOH STY (g/(l·h)) | Me₂O STY (g/(l·h)) | HCO₂Me STY (g/(l·h)) | EtOH STY (g/(l·h)) | CH₄ STY (g/(l·h)) | C₂H₆ STY (g/(l·h)) | AcOH STY (g/(l·h)) | MeOAc STY (g/(l·h)) | EtOAc STY (g/(l·h)) | MeC(O)H STY (g/(l·h)) |
|---|---|---|---|---|---|---|---|---|---|---|
| 82.9-101.2 hours Blocks 1 to 3 | 506 | 0 | 2 | 307 | 0.05 | 0.2 | 0.06 | 2 | 0.8 | 0.4 |
| 82.9-101.2 hours Block 4 | 1146 | 0.04 | 5 | 0.08 | 0.06 | 0 | 0 | 0 | 0 | 0 |
| 101.2-117.2 hours Blocks 1 to 3 | 1193 | 0.04 | 4 | 2 | 0.12 | 0.04 | 0 | 0.02 | 0.01 | 0 |
| 101.2-117.2 hours block 4 | 1095 | 0.07 | 6 | 0.07 | 0.06 | 0 | 0 | 0 | 0 | 0 |

Note -
The GC method used was not capable of distinguishing between ethane ($C_2H_6$) and ethane ($C_2H_4$), therefore the data provided for $C_2H_6$ is actually for $C_2H_6$ and $C_2H_4$ combined.
MeOH = methanol, Me₂O = dimethylether, HCO₂Me = methyl formate, EtOH = ethanol, AcOH = ethanoic acid, MeOAc = methyl acetate, EtOAc = ethyl acetate, MeC(O)H = Acetaldehyde

The invention claimed is:

1. A process for producing methanol and ethanol, wherein the methanol is produced from synthesis gas and the ethanol is produced via the hydrogenation of an ethanoic acid feed; characterised in that the hydrogenation of the ethanoic acid feed is carried out within the same alcohol synthesis unit and in the presence of the same catalyst(s) that is used to produce the methanol from the synthesis gas and wherein the feed introduced to the alcohol synthesis unit comprises synthesis gas and ethanoic acid.

2. Process according to claim 1, wherein the alcohol synthesis unit is operated at a temperature of more than 180° C.

3. Process according to claim 1, wherein the alcohol synthesis unit is operated at a temperature of less than 290° C.

4. Process according to claim 1, wherein the alcohol synthesis unit is operated at a pressure of more than 2 MPa.

5. Process according to claim 1, wherein the alcohol synthesis unit is operated at a pressure of less than 10 MPa.

6. Process according to claim 1, wherein the alcohol synthesis unit catalyst(s) is a methanol synthesis catalyst.

7. Process according to claim 1, wherein the alcohol synthesis unit catalyst(s) is a copper based catalyst.

8. Process according to claim 6, wherein the alcohol synthesis unit also comprises a hydrogenation catalyst selected from
   (i) a metal based catalyst, comprising of at least one metal from Group VIII of the periodic table and at least one metal chosen from rhenium, tungsten and/or molybdenum; and optionally an additional metal, that is capable of alloying with said Group VIII metal,
   (ii) a copper-based catalyst which is different from the methanol synthesis catalyst, and
   (iii) mixtures thereof.

9. Process according to claim 8, wherein the hydrogenation catalyst mixed with the methanol synthesis catalyst is a supported copper based catalyst, which is different from methanol synthesis catalyst, which comprises copper and at least one promoter supported on zinc oxide.

10. Process according to claim 1, wherein water represents between 0.5 and 20 mol % of the total liquid feed to the alcohol synthesis unit.

11. Process according to claim 1, wherein the ethanoic acid stream is vaporised prior to its introduction into the alcohol synthesis unit.

12. Process according to claim 1, wherein the feed mixture, including any recycle streams, entering the alcohol synthesis unit is more than 10° C. above its dew point temperature.

13. A process for the conversion of synthesis gas to ethanol, wherein the process comprises the following steps:

1) introducing synthesis gas and ethanoic acid into an alcohol synthesis unit to produce methanol and ethanol, wherein the methanol is produced from synthesis gas and the ethanol is produced via the hydrogenation of the ethanoic acid feed, and wherein the hydrogenation of the ethanoic acid feed is carried out within the same alcohol synthesis unit and in the presence of the same catalyst(s) that is used to produce the methanol from the synthesis gas,
2) separating the methanol from the ethanol of step 1,
3) introducing methanol, from step 2, and CO into a carbonylation unit in the presence of a methanol carbonylation catalyst, to produce ethanoic acid,
4) feeding ethanoic acid, produced in step 3, into the alcohol synthesis unit of step 1, and
5) recovering ethanol from step 2.

14. Process according to claim 13, wherein the process for the production of ethanoic acid by carbonylation of methanol comprises contacting methanol with CO, in a liquid reaction composition, in a carbonylation unit wherein the liquid reaction composition comprises:
   (a) ethanoic acid, (b) an iridium catalyst, (c) methyl iodide, (d) water and (e) at least one metal promoter.

15. Process according to claim 14, wherein the concentration of water in the liquid reaction composition of the carbonylation unit is in the range 0.1 to 15% by weight.

16. Process according to claim 14, wherein the iridium carbonylation catalyst concentration in the liquid reaction composition is in the range 100 to 6000 ppm by weight of iridium.

17. Process according to claim 14, wherein the metal promoter is selected from the group consisting of ruthenium, osmium, rhenium, cadmium, mercury, zinc, gallium, indium and tungsten, and is present in the liquid reaction composition at a molar ratio of promoter:iridium of [0.5 to 15]:1.

18. Process according to claim 14, wherein the concentration of methyl iodide in the liquid reaction composition is in the range 1 to 20% by weight.

19. Process according to claim 13, wherein the ethanoic acid stream is purified to remove carbonylation catalyst and water before its introduction into the alcohol synthesis unit.

20. Process according to claim 19, wherein the ethanoic acid stream contains less than 0.1 ppm wt of carbonylation catalyst.

21. Process according to claim 19, wherein the ethanoic acid stream contains less than 20 wt % of water.

22. A process for the conversion of a carbonaceous feedstock(s) into ethanol, wherein the process comprises the following steps:

1) introducing a carbonaceous feedstock into a synthesis gas reactor to produce a synthesis gas,
2) introducing synthesis gas, from step 1, and ethanoic acid into an alcohol synthesis unit to produce methanol and ethanol, wherein the methanol is produced from synthesis gas and the ethanol is produced via the hydrogenation of the ethanoic acid feed, and wherein the hydrogenation of the ethanoic acid feed is carried out within the same alcohol synthesis unit and in the presence of the same catalyst(s) that is used to produce the methanol from the synthesis gas,
3) separating the methanol from the ethanol of step 2,
4) introducing methanol, from step 3, and CO into a carbonylation unit in the presence of a methanol carbonylation catalyst, to produce ethanoic acid,
5) feeding ethanoic acid, produced in step 4, into the alcohol synthesis unit of step 2, and
6) recovering ethanol from step 3.

* * * * *